(12) United States Patent
Wick et al.

(10) Patent No.: US 12,045,981 B2
(45) Date of Patent: Jul. 23, 2024

(54) SYSTEMS AND METHODS FOR RADIOLOGIC AND PHOTOGRAPHIC IMAGING OF PATIENTS

(71) Applicant: CAMERAD TECHNOLOGIES, Decatur, GA (US)

(72) Inventors: Carson A. Wick, Decatur, GA (US); Srini Tridandapani, Decatur, GA (US)

(73) Assignee: CAMERAD TECHNOLOGIES, Decatur, GA (US)

( * ) Notice: Subject to any disclaimer, the term of this patent is extended or adjusted under 35 U.S.C. 154(b) by 0 days.

(21) Appl. No.: 17/942,052

(22) Filed: Sep. 9, 2022

(65) Prior Publication Data

US 2023/0055740 A1 Feb. 23, 2023

Related U.S. Application Data

(63) Continuation of application No. 16/734,255, filed on Jan. 3, 2020, now Pat. No. 11,468,562.

(60) Provisional application No. 62/788,059, filed on Jan. 3, 2019.

(51) Int. Cl.
  *G06T 7/00* (2017.01)
  *G06N 3/08* (2023.01)
  *G16H 50/20* (2018.01)

(52) U.S. Cl.
  CPC ............ *G06T 7/0012* (2013.01); *G06N 3/08* (2013.01); *G16H 50/20* (2018.01)

(58) Field of Classification Search
  CPC ..... G06T 7/0012; G06T 7/0014; G06T 7/337; G06T 2207/30016; G06T 7/90; G06T 2207/10088; G06T 2207/30004; G06T 2207/10024; G06T 2207/10081; G06T 2207/20128; G16H 30/20; G16H 30/40; G16H 50/20; G16H 50/70; G16H 10/60; G16H 10/65; G16H 20/40; G16H 40/67; G16H 15/00; G16H 50/50; G16H 70/60
  USPC ........................................................ 382/128
  See application file for complete search history.

(56) References Cited

U.S. PATENT DOCUMENTS

| | | | |
|---|---|---|---|
| 9,355,309 B2 | 5/2016 | Tridandapani et al. | |
| 2006/0109957 A1 | 5/2006 | Lutjens et al. | |
| 2010/0095340 A1 | 4/2010 | Ei et al. | |
| 2012/0159391 A1* | 6/2012 | Berry .................. | A61B 5/4824 715/823 |

(Continued)

FOREIGN PATENT DOCUMENTS

WO 2015/022430 A1 2/2015

OTHER PUBLICATIONS

International Preliminary Report on Patentability received for PCT Patent Application No. PCT/US2020/012265, mailed on Jul. 15, 2021, 6 pages.

(Continued)

*Primary Examiner* — Ajibola A Akinyemi
(74) *Attorney, Agent, or Firm* — Workman Nydegger

(57) ABSTRACT

Methods for co-registering images of different imaging modalities include obtaining a photograph and a medical image, maximizing mutual information between the photograph and the medical image, automatically locating features common to both the photograph and the medical image based on maximized mutual information between the photograph and the medical image, and automatically highlighting the located features within the photograph or medical image.

20 Claims, 2 Drawing Sheets

(56) References Cited

U.S. PATENT DOCUMENTS

| | | | |
|---|---|---|---|
| 2013/0177222 A1* | 7/2013 | Tridandapani | A61B 5/117 |
| | | | 382/128 |
| 2013/0279776 A1* | 10/2013 | Guissin | A61B 5/444 |
| | | | 382/128 |
| 2013/0320973 A1 | 12/2013 | Fenchel et al. | |
| 2016/0206203 A1 | 7/2016 | Yu et al. | |
| 2016/0313262 A1 | 10/2016 | Smilowitz et al. | |
| 2018/0328780 A1 | 11/2018 | Cochran | |
| 2019/0188850 A1 | 6/2019 | Reicher et al. | |
| 2019/0259481 A1* | 8/2019 | Chan | G16H 30/20 |
| 2020/0005481 A1 | 1/2020 | Mandwal et al. | |
| 2020/0035351 A1 | 1/2020 | Kim | |
| 2020/0160574 A1 | 5/2020 | Nye et al. | |

OTHER PUBLICATIONS

International Search Report and Written Opinion received for PCT Patent Application No. PCT/US2020/012265, mailed on Mar. 11, 2020, 7 pages.

Ramamurthy, et al., "A Novel Technology for Automatically Obtaining Digital Facial Photographs Near-Simultaneously with Portable Radiographs" Journal of Digital Imaging 28(3): 259-263, 2015.

Ramamurthy. S. et al., "Integrating Patient Digital Photographs with Medical Imaging Examinations," J Digit Imaging, vol. 26, Issue 5, 2013, pp. 875-885.

Search Report Written Opinion issued in PCT/US2020/012265 dated Mar. 11, 2020.

Ramamurthy Senthil et al: "Integrating Patient Digital Photographs with Medical Imaging Examinations", Journal of Digital Imaging, Springer International Publishing, Cham, vol. 26, No. 5, Oct. 1, 2013 (Oct. 1, 2013), pp. 875-885, XP002713104.

* cited by examiner

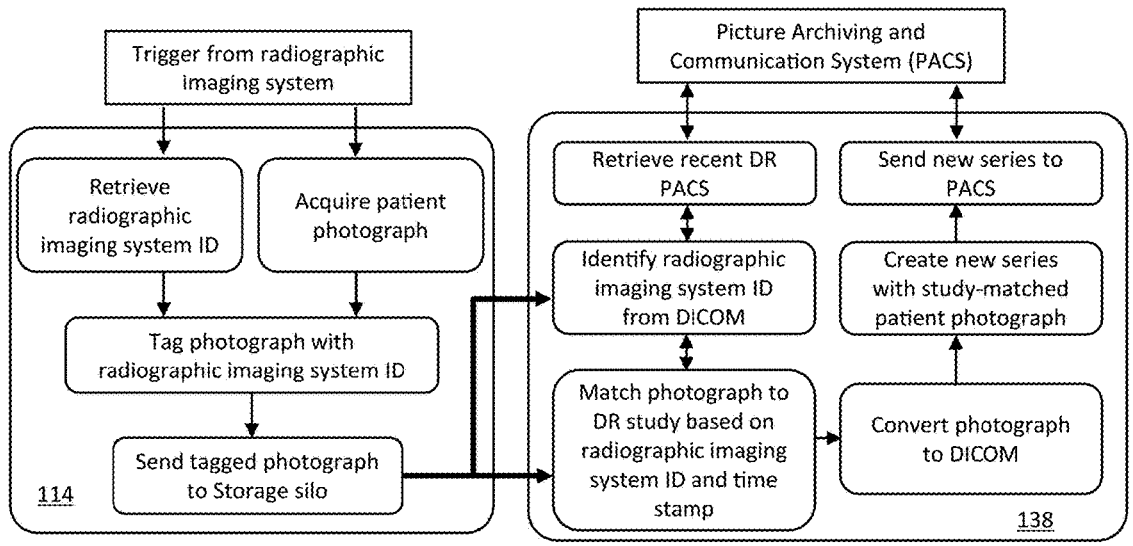
*FIG. 4*
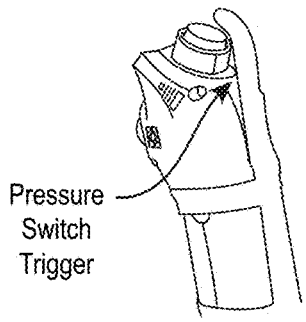
*FIG. 5*
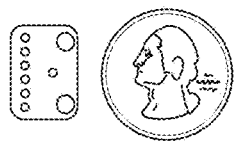
*FIG. 6A*
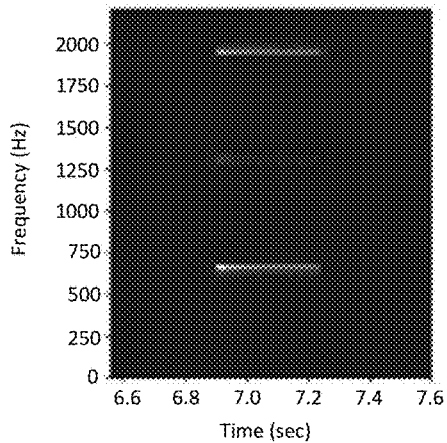
*FIG. 6B*
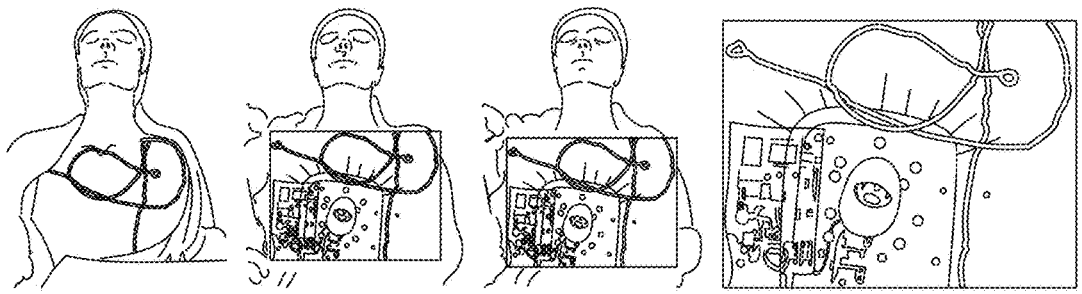
*FIG. 7A*  *FIG. 7B*  *FIG. 7C*  *FIG. 7D*

SYSTEMS AND METHODS FOR RADIOLOGIC AND PHOTOGRAPHIC IMAGING OF PATIENTS

CROSS-REFERENCE TO RELATED APPLICATIONS

This application is a continuation of U.S. patent application Ser. No. 16/734,255, filed Jan. 3, 2020 and entitled "SYSTEMS AND METHODS FOR RADIOGRAPHIC AND PHOTOGRAPHIC IMAGING OF PATIENTS," which claims priority to and the benefit of U.S. Provisional Patent Application Ser. No. 62/788,059, filed Jan. 3, 2019 and entitled "SYSTEMS AND METHODS FOR RADIOGRAPHIC AND PHOTOGRAPHIC IMAGING OF PATIENTS," both of which are incorporated herein by this reference in their entirety.

STATEMENT REGARDING FEDERALLY SPONSORED RESEARCH

The invention was made with government support under the Small Business Innovation Research, Phase I Award 1R43TR00229901A1 awarded by the National Institutes of Health/Center for Advancing Translational Sciences. The government may have certain rights in the invention.

BACKGROUND

Technical Field

This disclosure generally relates to radiologic and photographic imaging. More specifically, the present disclosure relates to systems and methods for acquiring and combining different forms of patient data, such as radiologic and photographic images, to improve the diagnosis, treatment, and/or capacity for accurately identifying and/or predicting disease states or other infirmities within a patient.

Related Technology

Advances in computing technology have resulted in a concomitant advance in medical device technologies, including within the field of diagnostic medicine. Particularly, the past century has demonstrated significant advances in medical imaging devices. Such advances have been hallmarked by the improvement and advent of new radiologic devices, such as radiography, computed tomography (CT), magnetic resonance imaging (MRI), and other radiologic imaging systems that allow for the non-invasive viewing and exploration of internal structures of the body. These medical imaging technologies allow physicians and clinicians to better document, diagnose, and treat pathologies.

Unfortunately, medical imaging studies are prone to mislabeling, such as associating the wrong demographic information (e.g., a different patient's name and medical record number) to a patient's imaging examination. Patient misidentification errors in medical imaging can result in serious consequences, such as the misdiagnosis of a disease state or the application of an inappropriate treatment regimen. Furthermore, the failure to properly associate a medical image study and patient identification may propagate to future imaging studies and negatively affect patient management decisions.

For example, an exemplary wrong-patient error case is illustrated in FIGS. 1A and 1B. The radiograph 100 illustrated in FIG. 1A is a radiograph obtained from a 43-year old black male following coronary artery bypass grafting and who has a left ventricular assist device and an implantable defibrillator. The patient presented with heart failure, and the healthcare personnel presumed the radiograph 102 illustrated in FIG. 1B to be a radiograph from the same patient captured at an earlier timepoint. However, the radiograph 102 of FIG. 1B is actually a radiograph of a 64-year old white male who had undergone bilateral lung volume reduction surgery for chronic obstructive pulmonary disease. Radiograph 102 of FIG. 1B was erroneously mislabeled as an earlier radiograph of the patient illustrated in radiograph 100 of FIG. 1. When presented to seasoned radiologists for diagnosis, 4 out of 4 readers failed to identify the mislabeling error and assumed that the patient had suffered a myocardial infarction and complications from surgery in the interim. In general, the nature of radiologic planar and cross-sectional images makes it difficult to correctly correlate radiologic medical images with patient details absent other identifying characteristics. As in the foregoing example, obvious age and racial differences between the patients of the mislabeled radiographs were completely lost or unobservable within the radiologic images, making it difficult for radiologists to identify the error.

A common, acceptable protocol for reducing mislabeling errors involves the verification of at least two patient identifiers (e.g., name, date of birth, social security number, or some hospital registration number) when radiologic images are being obtained. However, such verification may not always be possible, including with, for example, many trauma patients, patients who are unconscious or mentally unsound, and infants. Furthermore, even if a technician correctly gathers the requisite identifiers, it is difficult to verify with certainty that the identifiers have been properly associated with the patient. For example, the patient may have been given a mislabeled identification bracelet, or some other mislabeling error could occur before or after the point-of-care verification, that can lead to errors in the canonical two-parameter verification process.

Accordingly, there is a need to minimize or prevent mislabeling of radiologic images and to properly and consistently identify and/or correlate radiologic images with the correct patient, yet these and other disadvantages associated with radiologic imaging remain unaddressed.

BRIEF SUMMARY

Systems, methods, and apparatuses disclosed herein may solve one or more of the foregoing problems in the art of radiologic imaging. For example, a system for radiographic and photographic imaging of patients is disclosed herein and includes at least a first camera and a trigger electronically coupled to the first camera. The trigger can be operable to cause the first camera to capture one or more photographic images of a patient and can be associated with a manual button of a radiologic device that is operable to capture one or more planar or cross-sectional medical images of the patient.

In one aspect, the system additionally includes a second camera with the first camera being positioned on a first side of the radiologic device and the second camera being positioned on a second side of the radiologic device. Alternatively, the first and second cameras can be positioned on a same side of the radiologic device in a stereoscopic or non-stereoscopic arrangement. The camera can be coupled to or in close proximity to the radiologic device or positioned in the same room as the radiologic device.

In one aspect, the trigger causes the camera to capture the image substantially coincident in time with the radiologic device capturing one or more radiologic images.

In one aspect, the one or more cross-sectional medical images include one or more of an ultrasound image, radiographic image, mammogram, CT image, scintigraphy image, SPECT image, PET image, or MRI image.

In one aspect, the system includes a microphone and the trigger can be further configured to cause the camera to capture an image in response to the microphone receiving a predefined acoustic signal, in particular a tone or operating noise associated with the radiologic device.

In one aspect, the system includes a patient microphone for capturing an audio recording of the patient. The audio recording can optionally include one or more of an independent or complementary identifier of the patient or diagnostic information.

In one aspect, the system includes an infrared or thermal imaging camera. The system can include both an infrared and thermal imaging camera. Alternatively, the system can include both the camera for capturing light-based photographs and one of the infrared or thermal imaging camera. In either instance, the cameras can optionally be positioned stereoscopically relative to one another.

Aspects of the present disclosure additionally include methods of using the systems disclosed herein to identify a disease state in a patient, and can include at least the method acts of (i) compiling a dataset including a plurality of photographs of a plurality of patients, planar and cross-sectional image data associated with the plurality of patients, and one or more diagnoses or disease states associated with each unique subset of photographs and planar and cross-sectional image data for the plurality of patients; (ii) generating a deep learning convolutional neural network based on the dataset; (iii) identifying a set of predictive characteristics associated with at least some of the one or more diagnoses or disease states based on the deep learning convolutional neural network; (iv) using one or more aspects of the systems disclosed herein as to obtain a photograph and cross-sectional image data associated with a particular patient; (v) identifying characteristics within the photograph and cross-sectional image data corresponding to one or more disease states; and (vi) determining a disease state in the particular patient based on the identified characteristics. In one aspect, determining the disease state in the particular patient includes the acts of comparing the identified characteristics within the photograph and cross-sectional image data of the particular patient with the set of predictive characteristics and selecting a probable disease state based on the comparison.

In one aspect, the photograph data associated with the particular patient includes textual patient data on a patient information board and/or patient monitor, and the method can additionally include automatically extracting the textual patient data from the photograph data.

In one aspect, the method additionally includes the act of comparing the photograph and cross-sectional image data associated with the particular patient and adjusting the photograph data relative to the cross-sectional image data according to one or more of: scaling a size of the photograph, rotating the photograph, or adjusting a noise level, brightness, contrast, color, saturation, or opacity of the photograph.

In one aspect, the method additionally includes the act of administering a therapeutic regimen to the patient based on the determined disease state.

In one aspect, the method additionally includes the act of automatically detecting laterality of images of the planar and cross-sectional image data based on associated images of the photograph data. In one aspect, the method additionally includes comparing the detected laterality of images of the planar and cross-sectional image data to manually entered laterality data, and automatically flagging images having a mismatch between detected laterality and manually entered laterality.

Embodiments of the present disclosure can additionally include methods for automatically detecting a misidentified study and can include at least the steps of receiving and comparing photographs of a patient taken at a first and second timepoint and determining similarities between a subject depicted in the photographs based on patient representations obtained from a neural network model, or other facial recognition algorithm, trained using patient photographs and/or trained using general facial photographs. In one aspect, the patient representations are obtained from a neural network model trained using patient photographs. In another aspect, the patient representations are obtained from a facial recognition algorithm trained using general facial photographs. In one aspect, the detecting a misidentified study includes detecting a similarity value between the compared photographs that is less than a threshold similarity value, and the method additionally includes generating and sending an alert identifying the detected misidentified study.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which:

FIG. 4 illustrates an exemplary trigger system associated with a camera system and other computing system in electronic communication with the camera system, in accordance with one or more embodiments of the present disclosure;

FIG. 5 illustrates an exemplary trigger unit, in accordance with one or more embodiments of the present disclosure;

FIG. 6A illustrates an exemplary digital microphone for capturing audio data and/or for use as a trigger unit, in accordance with one or more embodiments of the present disclosure;

FIG. 6B illustrates a spectrogram of an alert tone recorded during X-ray acquisition from a portable X-ray unit, the spectrogram showing two pure tones lasting roughly 0.25 second being visible as having more power than surrounding audio (including talking), in accordance with one or more embodiments of the present disclosure; and FIGS. 7A-7D illustrate an exemplary co-registration of photographic and radiologic images where a patient photograph (FIG. 7A) can be co-registration with a radiologic image (FIG. 7B) such that non-anatomic artifacts can be identified and highlighted within the radiologic image (as shown in FIGS. 7C and 7D), in accordance with one or more embodiments of the present disclosure.

DETAILED DESCRIPTION

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments and is not necessarily intended to limit the scope of the claimed invention.

Overview and Exemplary Advantages of Disclosed Imaging Systems

As discussed above, wrong-patient errors in radiology—where one patient's imaging examination can be erroneously filed in another patient's record in the radiology picture archiving and communications system (PACS)—can lead to devastating consequences for both patients involved, as well as potential for healthcare provider liability for misdiagnosis and/or incorrect treatment. Embodiments of the systems and methods disclosed herein address at least some of the foregoing problems. For example, an imaging system can include a camera for point-of-care acquisition of patient photographs that can be associated with the radiologic medical image taken at the same time. These photos serve as intrinsic, externally visible, biometric identifiers, along with medical imaging studies. Embodiments of the present disclosure may additionally ensure that the photos are transmitted without any human intervention to the requisite PACS.

By leveraging a combination of timestamps and machine identifiers (e.g., an identifier associated with a particular radiographic imaging system), embodiments of the present disclosure may allow the photos to be added to the correct patients' imaging records within PACS. Additionally, implementing the disclosed systems in a clinical setting has clearly demonstrated that the presence of photographs significantly increases the detection rate of wrong-patient errors during interpretation of radiographs, specifically, and which may extend to radiologic images, generally. Surprisingly, the inventors have also shown that radiologists unexpectedly demonstrated a significant decrease in the amount of interpretation time when photographs were provided with radiographs of the corresponding patient.

Figure 1A:
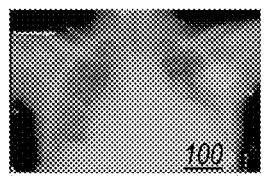
FIG. 1A and FIG. 1B each illustrate radiographs within a simulated wrong-patient error case.
Figure 1B:
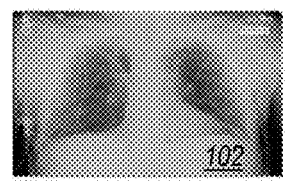
Figure 2A:
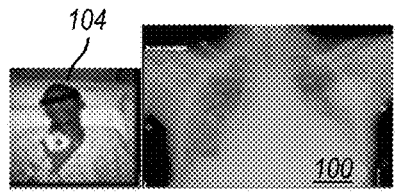
FIG. 2A and FIG. 2B respectively illustrate the radiographs of FIG. 1A and FIG. 1B along with redacted photographs of each corresponding patient taken at the time of the radiograph, the photographs being shown in association with the respective radiograph for each patient.
Figure 2B:
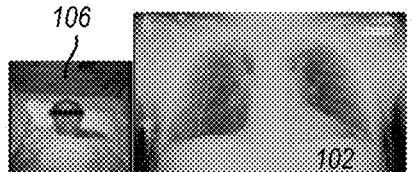

For example, regarding the wrong-patient error case discussed above (illustrated in FIGS. 1A and 1B), there is a reduced or eliminated wrong-patient error when implementing embodiments of the present disclosure. As shown in FIGS. 2A and 2B, a resultant combined and comparative image set can be seen where the radiograph 100 is associated with a photograph 104 of the patient taken at the same time as the radiograph 100 was captured. Similarly, radiograph 102 is properly associated with a photograph 106 taken of the patient at the same time as the radiograph 102 was captured and is not assumed to be an updated radiograph of radiograph 100. The photographs 104, 106 clearly illustrate that the radiographs 100, 102 are not from the same patient, and when presented to seasoned radiologists for diagnosis, 4 out of 4 readers were easily able to identify the simulated wrong-patient error instead of making an erroneous diagnosis.

Among other benefits, associating a photograph of the patient along with the captured radiologic image can reduce wrong-patient error by providing a set of easily verifiable identifying characteristics for the patient. As in the foregoing example, the obvious age and racial differences between the patients of the mislabeled radiographs are apparent given even a cursory observation. Such easily observable differences can extend to gender, body type, hair color, and other physical differences. Because the photograph can serve as identifying characteristics of the patient, it further enables misidentified radiographs to be associated with the correct patient. This is unprecedented since, in the past, misfiled radiologic images were usually discarded, implying that a patient had to undergo repeat imaging with its attendant radiation. Embodiments of the present disclosure can, therefore, reduce or eliminate the reimaging of patients whose radiologic images have been misfiled. This allows for extended utility of the radiologic device (as it can now be used for other non-repeated studies) and reduces patient exposure to potentially harmful radiation.

Additionally, associated photographs obtained by embodiments of the present disclosure can also provide image-related clinical context that positively impact diagnosis. In some examples, soft tissues abnormalities, which are not visible on the radiographs but are visible on the photographs, can be helpful in focusing the radiographic interpretation of the underlying bone. In other examples, the wide-angle lens used by some disclosed camera systems can capture the patient monitors in the hospital room, which provide more information to the radiologist—information that would have taken the interpreting radiologist several steps of wading through the patient's electronic medical record to find. In some instances, facial features of patients who have suffered acute strokes may clearly point to the underlying diagnosis. In other instances, the photographs may clearly show whether the patient was upright or lying flat—information that was not visible on the corresponding radiologic image. This positioning information can be critical to the interpreting radiologist, for example, when excluding the presence of free air in the abdomen, which is an ominous sign that can suggest perforated bowel and can dramatically increase the efficiency and confidence of radiologic image interpretation.

Additionally, as described in more detail below, embodiments of the present disclosure can enable the rapid identification of various non-anatomic features present in radiologic images (e.g., feeding tubes, endotracheal tubes, wires for monitoring patient vitals, or other tubes and wires), which can allow the radiologist to more efficiently discriminate between important and non-important features in radiologic images. Such non-anatomic features can also provide useful information of the type of care that is being or has been provided to the patient and/or provide additional indications as to the physical condition of the patient.

The embodiments disclosed herein provide radiologists with additional patient identification in the form of a photograph (e.g., of the face and chest obtained at the point-of-care with portable radiography). The inventors have demonstrated that systems disclosed herein that include a camera system for capturing a patient's photograph prior to and/or during radiography improved radiologists' ability to detect wrong-patient errors, in some instances, by about 5-fold. Surprisingly, adding the patient's photo to the radiological image was also shown to reduce the radiologist's interpretation time of the corresponding radiographs. Thus, in addition to decreasing wrong-patient errors, the systems and methods disclosed herein beneficially enable an increase interpretation efficiency, thereby decreasing interpreting physician cost—a substantial portion of the cost of an imaging study. In addition, patient photographs can increase empathy and satisfaction among interpreting radiologists, resulting in improved patient-centered radiology care.

Additional features and advantages of the disclosure will be set forth in the description that follows and will be obvious, at least in part, from the description or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

Exemplary Systems for Radiographic and Photographic Imaging

As provided herein, embodiments of the present disclosure can include systems and apparatuses for radiographic and photographic imaging of patients. For example, as shown in FIG. 3, a medical imaging and archiving system 110 for radiographic and photographic imaging of patients can include a radiographic imaging system 112 and a camera system 114 operable to generate medical images and photographic images of a patient, respectively, to prevent and/or reduce the occurrence and/or likelihood of patient misidentification errors, among other benefits disclosed herein.

In accordance with embodiments of the present disclosure, medical images may be generated at the system 110 by one or more medical imaging modalities, including any known medical imaging modality or combination of modalities, and may be generated by any known medical imaging device or system. For example, the medical imaging modality used by the system 110 may include, but is not necessarily limited to: ultrasound, radiography, mammography, computed tomography (CT), computed tomography perfusion (CTP), scintigraphy, single-photon emission computed tomography (SPECT), positron-emission tomography (PET), and magnetic resonance imaging (MM).

Figure 3:
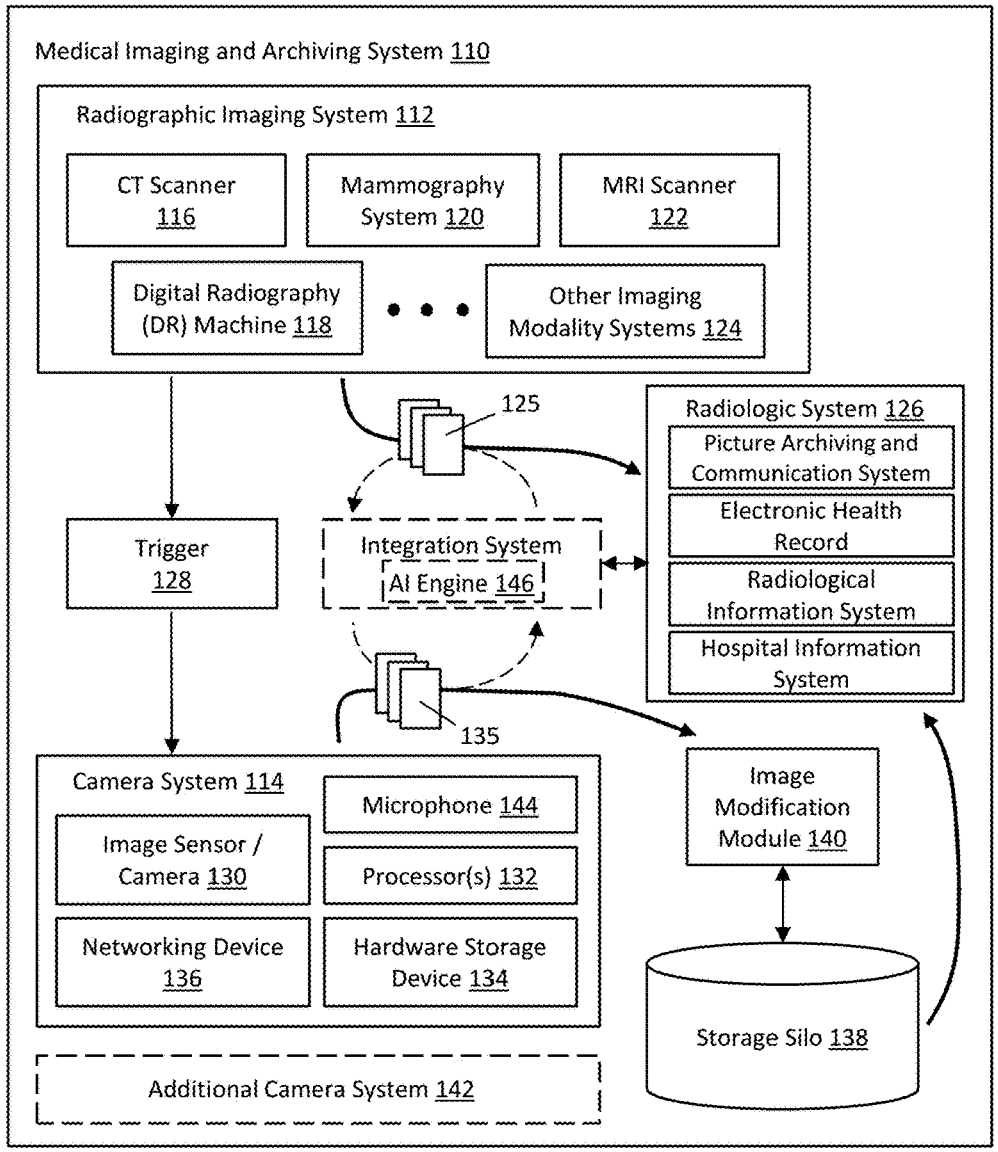
FIG. 3 illustrates an exemplary system having a camera system associated with a radiographic imaging system, in accordance with one or more embodiments of the present disclosure.

As shown in FIG. 3, the imaging modality can be implemented by a radiographic imaging system 112 configured to generate medical images and may include a radiologic device that generates one or more planar or cross-sectional images (i.e., radiologic images 125) in the form of an ultrasound image, radiographic image, mammogram, CT image, CTP image, scintigraphy image, SPECT image, PET image, or MRI image, respectively. With continued reference to FIG. 3, a radiographic imaging system 112 can include one or more of a CT scanner 116, a digital radiography (DR) machine 118, a mammography system 120, an MRI scanner 122, or other imaging modality system 124 known in the art (e.g., an ultrasound device, a stationary X-ray machine, a scintigraphy device such as a scintillation camera, a SPECT scanner, a PET scanner, or similar)—any of which may be coupled to an image processing, computing, and/or storage system, such as PACS or other component of radiologic system 126.

The medical imaging and archiving system 110 can additionally include a camera system 114 operable to take photographs of the patient or subject being imaged by the radiographic imaging system 112 and a trigger 128 in electronic communication with the camera system 114. In some embodiments, the camera system 114 and trigger 128 can be controlled by one or more components of the camera system 114 and/or radiographic imaging system 112. This can include, for example, controlling the timing and number of pictures captured by these systems 112, 114.

In some embodiments, the camera is coupled directly to the radiologic device, or it may be positioned in the same room as, or in the vicinity of, the radiologic device. For example, the camera system can include an image sensor or camera 130 associated with and/or operated by a computing system. As shown in FIG. 3, the computing system associated with the image sensor or camera 130 can include one or more processors 132 and memory (e.g., a hardware storage device 134). In some embodiments, the camera can be operated by a single-board computer, such as a Raspberry Pi or similar compact computing system, and can be configured to communicate with peripheral devices and/or a network through the onboard (or associated) networking device 136. The camera system 114 can additionally process and temporarily (or permanently) store the captured images. In some embodiments, however, the images 135 captured by the camera system 114 can be transmitted (e.g., via a wired or wireless signal through networking device 136) to a storage silo 138 or integration system, which in some embodiments may be the same system or subsystem, where the photographs are processed and/or temporarily stored. In some embodiments, the images 135 captured by the camera system 114 can be processed and temporarily stored before being transferred to and stored within an archive, such as PACS or other component of radiologic system 126.

The photos captured at the camera system 114 serve as intrinsic, externally visible, biometric identifiers, along with medical imaging studies. After being captured at the camera system, the images 135 are timestamped and associated with a machine identifier that indicates which radiographic imaging system was used to capture an analogous medical image of the patient. This can be performed, for example, at the camera system 114 (e.g., by executing, at the processor(s) 132, computer-executable instructions stored on the hardware storage device 134 that configure the camera system to timestamp and/or update the metadata associated with the captured image to include a timestamp and the machine identifier associated with the image). An exemplary method flow of such is provided in FIG. 4.

Alternatively, the images can be transferred to an image modification module 140 configured to tag the images with identifying information, such as a timestamp and machine identifier. In some embodiments, the image modification module 140 is associated with the storage silo 138, as shown in FIG. 3 or may alternatively be associated with the camera system (not shown). The image modification module 140 can beneficially ensure that the images are properly identifiable such that, when transferred to PACS or other component of radiologic system 126, the images are added to the correct patient's imaging records within PACS or other component of radiologic system 126.

In some embodiments, the trigger 128 or switch associated with the medical imaging and archiving system 110 can be associated with a manual button on a controller configured to capture one or more cross-sectional images of the patient. This can include, for example, integrating the trigger into a manual controller associated with the radiographic imaging system 112 such that operating the manual controller to capture a radiologic image of the patient using the radiographic imaging system 112 activates the trigger and causes the camera to capture a photograph of the patient and optionally the patient's surroundings.

Accordingly, activating the camera can cause the camera to capture a photograph of the patient substantially coincident with capturing one or more radiologic images from the radiologic device. Additionally, or alternatively, activating the camera can cause the camera to capture the photograph prior to or after capturing the radiologic images.

It should be appreciated that the patient image may be a portrait of the patient or an image of any portion of a patient's body. The patient image may be confined to the face of a patient, from about the forehead to the chin, or may include additional portions of a patient's body, such as the upper chest area of the patient. Additionally, or alternatively, the patient image may include the area of the patient for which the medical image is obtained. It will be appreciated that multiple photographs showing different patient views can be captured. For example, the system can be configured to image the patient prior to and/or after imaging with the radiographic imaging system, such as when the patient is being prepared for or removed from a CT or MRI scanner. In some instances, the photograph of the patient is taken at the same time or substantially the same time as the radiograph is being taken. This can beneficially allow the radiologist to match the body position between the cross-sectional medical image and the photograph as a fast and efficient confirmation that there likely has not been a patient misidentification or laterality errors.

In some embodiments, the patient image may be still or dynamic. The selection of a still or dynamic image may be controlled by the user or be automatic. Accordingly, the patient image may be a digital photograph or a digital video, and the selection or determination of a still or dynamic image capture may be preset or selectable by the imaging technician, a physician, or another healthcare provider. The patient image may be captured and/or stored in any known digital format. For example, the format may be chosen from any of JPEG, TIFF, PNG, GIF, BMP, WAV, AVI, FLV, MJ2, MPEG, MPEG-2, MP4, WMV, ASF, or QTFF. In some embodiments, the file format may be selected according to standards for transmitting radiological or other medical information, such as DICOM format, although if the patient image is obtained in a format other than the format of the medical record storage system, such as DICOM, the patient image may be later converted.

Furthermore, the format of the patient image may depend on the medical imaging device configuration. For example, a patient imaging device configured to obtain a still or dynamic patient image may be integrated with the medical imaging device. Alternatively, a patient imaging device configured to obtain a still or dynamic image of the patient may be a peripheral device. In either case, the patient image may be obtained by a digital camera operable to capture photographs and/or video. As a non-limiting example of the foregoing, the patient image may be obtained by a charge-coupled device or a complementary metal oxide semiconductor (CMOS) camera. The camera may be operable to capture images within the visible or infrared light spectra or may capture thermal images. In some embodiments, the infrared and/or thermal imaging camera is separate from the visible light camera and may be positioned relative thereto stereoscopically, as discussed in more detail below.

In some embodiments, the camera system includes a camera having a wide-angle lens. The use of wide-angle lenses beneficially allows for the acquisition of potentially relevant information in the patient's room. For example, if there is a whiteboard in the patient's room behind the patient with information such as phone number, patient location (room), physician name, nurse name, etc., this information can be used by the interpreting doctor (e.g., radiologist) to contact the appropriate physician or nurse without having to look up this information elsewhere. Additionally, if the patient monitor, which has information such as heart rate, blood pressure, respiratory rate, pulse oximetry, etc., is placed within the field of the wide-angle lens, then this information can also be seen while interpreting the radiographs and can help inform the interpretation. It should be appreciated that in some embodiments, automated image analysis can be performed on captured photographs to extract contextual information from the patient's environment and transmit it to the electronic medical record separately.

The use of different photographic imaging modalities, such as visible light photography, infrared photography, and/or thermal photography can serve multiple beneficial purposes. For example, in low-light scenarios, photographs taken in the visible light spectrum may have too much noise in the darker portions of the photograph whereas infrared photography may beneficially be better suited to capture a higher fidelity photo of the patient for identification, verification, and/or diagnostic purposes. Additionally, thermal imaging can be incorporated into camera systems disclosed herein as a beneficial way to gather additional, potentially useful information. For example, thermal imaging can be used to identify "hot spots" on the patient's body, which would indicate localized inflammation and/or infection that can be correlated with the medical images captured by the radiographic imaging system.

In some embodiments, low-light performance can be improved by including a camera without an infrared (IR) filter and with LED IR illumination. The IR LEDs cast a light that is invisible to the naked eye but is visible to an IR filterless camera. Because it is preferable to have an image with IR removed when possible, a dual camera solution can be implemented for portable X-ray and other low-light applications. For example, when the overall brightness of the normal image is above a threshold, the visible light image may be used, whereas, when the brightness is below that threshold, the IR image may be used.

Additionally, or alternatively, the imaging systems disclosed herein can include additional camera systems 142 that are each operable to capture images of the patient (e.g., at different positions or angles and/or in different imaging modalities). In some embodiments, multiple cameras or camera systems can provide significant additional benefits. For example, for a mammography system, the patient's face may be on one side of the machine while the opposing breast is imaged. In this situation, two cameras may be particularly useful—one on each side of the machine. If each camera is configured to image the patient at the same time the breast is being imaged, at least one of the cameras will capture a photograph of the patient's face. Knowing which camera captured the patient's face can inform which breast was being imaged. To assist in this, each photograph may be tagged with metadata identifying the camera or camera location used to capture the image, which can then be used to infer or determine laterality. Accordingly, multiple cameras can beneficially enable documenting of laterality and avoid or reduce laterality errors (e.g., errors documenting left versus right side of patient). Additionally, in some embodiments, the system is configured to automatically detect laterality (e.g., left, right) and/or position (e.g., face up, face down, feetfirst, headfirst). The detected information can, in some embodiments, be automatically added to the image header and/or PACS (or other hospital system), and this information may, in some instances, be used to automatically compare against what was entered by the technologist and raise an alert if there is a discrepancy between the two. This can beneficially reduce potential misidentification errors and act as another layer of verification and safety. It should be appreciated that the determination of laterality and/or position can be automatically determined following supervised training of an artificial intelligence engine, such as the artificial intelligence engine 146 of the integration system in FIG. 3.

In some embodiments, the integration system, which can include an artificial intelligence engine 146, and/or the image modification module 140 can be independent of the camera system 114 and could be used with photographs already existing in the radiologic system 148. Additionally, in some embodiments, direct integration between the radiologic modality and photographs obtained by the camera system 114 or third party system and the integration system (or components thereof, such as PACS) can be implemented.

In another exemplary embodiment, a camera can be positioned on each side of the CT gantry, which can increase the likelihood that the patient's face is captured regardless of whether the patient goes into the gantry headfirst or feet first. In some embodiments, one camera may be used and positioned on the side of the gantry associated with the patient position found in the majority of CT images. In some embodiments, the camera is on a track and can automatically identify a patient orientation and position itself along the track to place the patient's face within the viewing area of the camera. This can include a linear track along a longitudinal axis of the gantry (e.g., to capture a photograph of the patient's face in a feet-first or head-first orientation) and/or an orbital track around the gantry (e.g., to capture a photograph of the patient's face in a prone or supine orientation).

As discussed above, the trigger 128 can be a manual trigger or mechanical switch responsive to the activation of the radiographic imaging system by the technician or attending healthcare provider (e.g., as shown in FIG. 5). In some embodiments, the trigger may be operable to automatically capture the photograph for optimal performance and reliability.

For example, one method to automatically trigger photo acquisition includes incorporating a split-core current sensor as a switch and thereby be completely decoupled from the technologist. The split-core variety of a current sensor can be non-intrusively clipped around the cable supplying current to the X-ray filament. While resulting tube currents are in the mA range, the supply current is high enough to be sensed by sensors (e.g., HCT Series Current Transducer). The sensor may generate either a detectable voltage or current that may be used to trigger the camera system to acquire a photo of the patient when the X-ray tube is emitting. In some embodiments, the current sensor can be powered by the camera system. As a result, a separate step-up circuit, and potentially a battery power supply if needed, may be implemented. It should be appreciated that in some embodiments, the current-sensing trigger can be configured to be tunable to different sensed amperages, allowing the same switch design to be used for different radiology machines. One advantage of this approach includes potentially increased reliability as other automatic triggers disclosed herein can be more resource intensive and/or have signal processing steps that occur at the camera system.

As an additional example, and with continued reference to FIG. 3, a camera system 114 can include a microphone 144 (or other transducer) operable to automatically trigger photograph acquisition by the camera system 114. One such exemplary embodiment of a microphone is shown in FIG. 6A. In some embodiments, the microphone acts as a trigger, causing the camera to capture a photograph in response to the microphone receiving a predefined acoustic signal.

The predefined acoustic signal can be any acoustic signal. For example, the predefined acoustic signal can include a tone or operating noise associated with a radiologic device. In an exemplary embodiment, as illustrated in FIG. 6B, the predefined acoustic signal can include an alert tone recorded during X-ray acquisition from a portable X-ray unit. FIG. 6B illustrates a spectrogram of such an exemplary alert tone. The spectrogram shows two pure tones lasting roughly 0.25 sec visible as having more power than surrounding audio (including talking).

Upon detecting this tone, the camera system may take a photograph of the patient. Audio data may be buffered and its frequency content analyzed for the presence of the tone. In some embodiments, a module may be added to the software framework of the imaging system to train and incorporate a library of detectors for known radiology machine models. With this software structure, the detector can be modified for each model of radiography unit. The advantages of this triggering approach include the ease of integration, adaptability, and the dual-use of the microphone, which may also be used to record the patient's voice to provide further patient identification and clinical information.

In some embodiments, the camera can capture an image or a series of time-lapsed or dynamic images, such as a video recording. Video data can beneficially provide additional correlated facial images that can enhance facial recognition algorithms. A brief video clip providing the patient's chief complaint directly from the patient embedded with the radiographs can also beneficially speed up the interpretation and add to radiologists' confidence in the interpretation.

Additionally, or alternatively, an audio recording of the patient can be captured. This audio can be used to further serve as an independent or complementary identifier of the patient. For example, a patient may be asked to state their name while or just before the radiologic images are obtained. This audio can also be used to obtain, for example, survey information from patients. In some embodiments, the survey information can be uniquely tied to the radiologic imaging study and can be used, for example, as an analytic tool to improve service performance within the imaging department.

In some embodiments, the audio can be used as diagnostic information. For example, slurring of speech can be indicative of a stroke, and this information can be combined with the photographic or radiologic imaging to improve diagnosis. Similarly, video recordings can reveal heart rate information since subtle rhythmic facial hue changes with the beating heart can be detected by advanced image processing. As another example, patients can answer simple questions about their chief complaint and these answers can be stored along with the imaging examination. These answers may provide interpreting radiologists with the critical information regarding the reason (indication) for the examination and thus impact the interpretation. Quite often the reasons for the examination given on the requisition, i.e., order, for the imaging study are vague since they may be generic summaries based on billing codes, rather than clinically relevant information.

Audio and/or video can also be used as a record of the informed consent for the radiologic procedure. Video and audio content may be leveraged to improve and/or supplement both facial recognition and clinical context provided to the radiologist. In addition, text of radiology exam speech may be stored within the hospital information system.

Methods for Standardizing Image Storage and Display

Photographs captured using the foregoing imaging systems can be incorporated into methods for standardizing image storage and display. As a non-limiting example, an exemplary method can include the method acts of (i) acquiring or receiving a photograph of a patient from a camera or storage silo containing said photograph, (ii) acquiring or receiving one or more planar or cross-sectional images of the patient from a radiologic device or storage silo containing said cross-sectional images, (iii) comparing the photograph and the one or more cross-sectional images; and (iv) adjusting the photograph relative to the one or more cross-sectional images. In some embodiments, acquiring the photograph includes capturing the photograph using any of the systems for radiographic and photographic imaging of patients disclosed herein. Additionally, adjusting the photograph relative to the cross-sectional images can include scaling a size of the photograph, rotating the photograph, adjusting a brightness, contrast, color, saturation, or opacity of the photograph, or combinations thereof and may be implemented using a machine learning model or other facial recognition algorithm.

For example, autorotation performance may be improved by training a convolutional neural network (CNN) to output the correct rotation given a patient photo of unknown rotation. In one embodiment, autorotation can be accomplished by performing CNN face detection on each of the four possible rotations. If a face is detected in more than one of the rotations, the rotation with the largest response is assumed correct. There are two downsides to this approach: (1) it can be relatively time consuming, taking about 20 seconds per photograph, and (2) it relies on face detection, which can be difficult to detect in extremely low-light conditions or when a medical apparatus is obscuring the face of the patient. By training an autorotator specifically for autorotation, calculation time can be decreased while also increasing accuracy.

As an additional example, methods can include identifying and/or verifying a patient's identity based on photographs taken of the patient at multiple timepoints and/or within multiple frames of a video. Such methods can automatically eliminate or flag mislabeled or mismatched images thereby reducing wrong-patient errors.

Systems for Automated Registration of Corresponding Photographs and Radiology Images A system that automatically registers and aligns corresponding photographs and radiographs is needed for proper clinical display and also to leverage the mutual information present in both for machine learning and computer vision applications.

Accurate multi-modal image registration of the larger patient photograph around a simultaneously acquired radiograph relies primarily on three characteristics: rotation, translation, and scale. Skew may not be considered because the radiograph and photograph have the same image plane, i.e., they are pointed in roughly the same direction. Embodiments of the present disclosure include systems and methods for automated registration of corresponding photographs and radiology images. In one embodiment, multi-modal image registration techniques are used to maximize the mutual information between two given images of different modalities and thereby allow for the identification of rotation, translation, and scale between photographs and radiographs. For example, as shown in FIGS. 7A and 7B, a radiograph of the patient is rotated, translated, and scaled over a photograph of the patient such that the photograph and radiology image are co-registered.

A system that automatically indicates external, non-anatomic features present in radiology images, such as lines and tubes, may allow the radiologist to more efficiently discriminate between important and nonimportant features in radiology images. In some embodiments, systems and methods disclosed herein further enable the automatic annotation of external features in radiology images. An exemplary method includes the act of locating external features common to both the photograph and radiograph. This may be accomplished either by region-based correlation techniques (regions of high correlation correspond to common features) or as regions of large mutual information. As shown in FIG. 7C, the external features common to both the photograph and radiograph are located.

After being located, the presentation of these annotated external features is refined by improving the color, opacity, size, etc. to maximize the utility of these annotations. As a result, photographs may be spatially registered to the corresponding radiographs, allowing for accurate display and increasing the future usefulness of point-of-care photographs in informatics and machine learning contexts. The location of external features such as lines and tubes may be automatically annotated and recorded in a manner conducive to conveying location information to radiologists directly on radiographs.

Methods for Identifying a Disease State in a Patient

The systems disclosed herein may additionally be implemented within methods for identifying a disease state in a patient. Particularly, a combination of photographic and radiographic characteristics may be identified as correlating with a disease state, and these characteristics may be elucidated using a machine learning model and applied to identify, predict, and/or treat patients by administering a (prophylactic or reactionary) therapeutic regimen based on the identified/predicted disease state.

For example, a method for identifying a disease state in a patient can include the method acts of (i) acquiring a photograph and cross-sectional image data associated with a patient, (ii) identifying characteristics within the photograph and cross-sectional image data corresponding to one or more disease states, and (iii) determining a disease state in the patient based on the identified characteristics. Methods may additionally include acts of (iv) compiling a dataset, (v) generating a deep learning convolutional neural network based on the dataset, and (vi) identifying a set of predictive characteristics associated with at least some of the diagnoses or disease states, based on the deep learning convolutional neural network. The dataset compiled in act (iv) above can include, for example and among other things, a plurality of photographs of a plurality of patients, planar and cross-sectional image data associated with the plurality of patients, and one or more diagnoses or disease states associated with each unique subset of photographs and cross-sectional image data for the plurality of patients.

In some embodiments, determining the disease state in the patient can include comparing the identified characteristics within the photograph and planar or cross-sectional image data with the set of predictive characteristics and selecting a probable disease state based on the comparison. Additionally, or alternatively, the methods can include administering a therapeutic regimen to the patient based on the determined disease state.

Additionally, in some embodiments, patient photographs can be used to allow for an automated method of visually assessing patient well-being. The automated assessment can, for example, provide a quantitative measure of how "healthy" the patient looks. These measures can be correlated with the medical imaging studies over time with deep learning so that the appearance of the patient can potentially provide a diagnosis or diagnostic clues.

Abbreviated List of Defined Terms

To assist in understanding the scope and content of the foregoing and forthcoming written description and appended claims, a select few terms are defined directly below.

The term "healthcare provider" as used herein generally refers to any licensed and/or trained person prescribing, administering, or overseeing the diagnosis and/or treatment of a patient or who otherwise tends to the wellness of a patient. This term may, when contextually appropriate, include any licensed medical professional, such as a physician (e.g., Medical Doctor, Doctor of Osteopathic Medicine, etc.), a physician's assistant, a nurse, a radiology technician, a dentist, a chiropractor, etc. and includes any physician specializing in a relevant field (e.g., radiology).

The term "patient" generally refers to any animal, for example a mammal, under the care of a healthcare provider, as that term is defined herein, with particular reference to humans under the care of a primary care physician, oncologist, surgeon, or other relevant medical professional. For the purpose of the present application, a "patient" may be interchangeable with an "individual" or "person." In some embodiments, the individual is a human patient.

As used herein, the term "patient information board" refers to an environmental object in the vicinity of the patient and which has associated therewith patient information (e.g., name, date of birth, patient ID, medications, allergies, medical history, vitals, etc.) or other information relevant to the patient's treatment, diagnosis, or medical history, such as the name and/or contact information of healthcare providers tending to the patient, symptoms, prior illnesses or procedures, or similar. It should be appreciated that the term "patient monitor" can include any of the foregoing information associated with a patient information board but provided on an electronic display or device, such as a vital monitoring system, tablet, or similar.

The term "physician" as used herein generally refers to a medical doctor, and particularly a specialized medical doctor, such as a radiologist, oncologist, surgeon, primary care physician, or other specialized medical doctor interpreting or viewing radiologic images. This term may, when contextually appropriate, include any other medical professional, including any licensed medical professional or other healthcare provider, such as a physician's assistant, a nurse, a veterinarian (such as, for example, when the patient is a non-human animal), etc.

Computer Systems of the Present Disclosure

It will be appreciated that computer systems are increasingly taking a wide variety of forms. In this description and in the claims, the term "computer system" or "computing system" is defined broadly as including any device or system—or combination thereof—that includes at least one physical and tangible processor and a physical and tangible memory capable of having thereon computer-executable instructions that may be executed by a processor. By way of example, not limitation, the term "computer system" or "computing system," as used herein is intended to include personal computers, desktop computers, laptop computers, tablets, hand-held devices (e.g., mobile telephones, PDAs, pagers), microprocessor-based or programmable consumer electronics, minicomputers, mainframe computers, multi-processor systems, network PCs, distributed computing systems, datacenters, message processors, routers, switches, and even devices that conventionally have not been considered a computing system, such as wearables (e.g., glasses).

The memory may take any form and may depend on the nature and form of the computing system. The memory can be physical system memory, which includes volatile memory, non-volatile memory, or some combination of the two. The term "memory" may also be used herein to refer to non-volatile mass storage such as physical storage media.

The computing system also has thereon multiple structures often referred to as an "executable component." For instance, the memory of a computing system can include an executable component. The term "executable component" is the name for a structure that is well understood to one of ordinary skill in the art in the field of computing as being a structure that can be software, hardware, or a combination thereof.

For instance, when implemented in software, one of ordinary skill in the art would understand that the structure of an executable component may include software objects, routines, methods, and so forth, that may be executed by one or more processors on the computing system, whether such an executable component exists in the heap of a computing system, or whether the executable component exists on computer-readable storage media. The structure of the executable component exists on a computer-readable medium in such a form that it is operable, when executed by one or more processors of the computing system, to cause the computing system to perform one or more functions, such as the functions and methods described herein. Such a structure may be computer-readable directly by a processor—as is the case if the executable component were binary. Alternatively, the structure may be structured to be interpretable and/or compiled—whether in a single stage or in multiple stages—so as to generate such binary that is directly interpretable by a processor.

The term "executable component" is also well understood by one of ordinary skill as including structures that are implemented exclusively or near-exclusively in hardware logic components, such as within a field programmable gate array (FPGA), an application specific integrated circuit (ASIC), Program-specific Standard Products (ASSPs), System-on-a-chip systems (SOCs), Complex Programmable Logic Devices (CPLDs), or any other specialized circuit. Accordingly, the term "executable component" is a term for a structure that is well understood by those of ordinary skill in the art of computing, whether implemented in software, hardware, or a combination thereof.

The terms "component," "service," "engine," "module," "control," "generator," or the like may also be used in this description. As used in this description and in this case, these terms whether expressed with or without a modifying clause—are also intended to be synonymous with the term "executable component" and thus also have a structure that is well understood by those of ordinary skill in the art of computing.

While not all computing systems require a user interface, in some embodiments a computing system includes a user interface for use in communicating information from/to a user. The user interface may include output mechanisms as well as input mechanisms. The principles described herein are not limited to the precise output mechanisms or input mechanisms as such will depend on the nature of the device. However, output mechanisms might include, for instance, speakers, displays, tactile output, projections, holograms, and so forth. Examples of input mechanisms might include, for instance, microphones, touchscreens, projections, holograms, cameras, keyboards, stylus, mouse, or other pointer input, sensors of any type, and so forth.

Accordingly, embodiments described herein may comprise or utilize a special purpose or general-purpose computing system. Embodiments described herein also include physical and other computer-readable media for carrying or storing computer-executable instructions and/or data structures. Such computer-readable media can be any available media that can be accessed by a general purpose or special purpose computing system. Computer-readable media that store computer-executable instructions are physical storage media. Computer-readable media that carry computer-executable instructions are transmission media. Thus, by way of example—not limitation—embodiments disclosed or envisioned herein can comprise at least two distinctly different kinds of computer-readable media: storage media and transmission media.

Computer-readable storage media include RAM, ROM, EEPROM, solid state drives ("SSDs"), flash memory, phase-change memory ("PCM"), CD-ROM or other optical disk storage, magnetic disk storage or other magnetic storage devices, or any other physical and tangible storage medium that can be used to store desired program code in the form of computer-executable instructions or data structures and that can be accessed and executed by a general purpose or special purpose computing system to implement the disclosed functionality of the invention. For example, computer-executable instructions may be embodied on one or more computer-readable storage media to form a computer program product.

Transmission media can include a network and/or data links that can be used to carry desired program code in the form of computer-executable instructions or data structures and that can be accessed and executed by a general purpose or special purpose computing system. Combinations of the above should also be included within the scope of computer-readable media.

Further, upon reaching various computing system components, program code in the form of computer-executable instructions or data structures can be transferred automatically from transmission media to storage media (or vice versa). For example, computer-executable instructions or data structures received over a network or data link can be buffered in RAM within a network interface module (e.g., a "NIC") and then eventually transferred to computing system RAM and/or to less volatile storage media at a computing system. Thus, it should be understood that storage media can be included in computing system components that also—or even primarily—utilize transmission media.

Those skilled in the art will further appreciate that a computing system may also contain communication channels that allow the computing system to communicate with other computing systems over, for example, a network. Accordingly, the methods described herein may be practiced in network computing environments with many types of computing systems and computing system configurations. The disclosed methods may also be practiced in distributed system environments where local and/or remote computing systems, which are linked through a network (either by hardwired data links, wireless data links, or by a combination of hardwired and wireless data links), both perform tasks. In a distributed system environment, the processing, memory, and/or storage capability may be distributed as well.

Those skilled in the art will also appreciate that the disclosed methods may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Although the subject matter described herein is provided in language specific to structural features and/or methodological acts, it is to be understood that the subject matter defined in the appended claims is not necessarily limited to the described features or acts so described. Rather, the described features and acts are disclosed as example forms of implementing the claims.

CONCLUSION

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatuses disclosed herein may be made without departing from the scope of the disclosure or of the invention. Thus, while various aspects and embodiments have been disclosed herein, other aspects and embodiments are contemplated. All changes that come within the meaning and range of equivalency of the claims are to be embraced within their scope.

EXAMPLES

The following examples as set forth herein are intended for illustrative purposes only and are not intended to limit the scope of the disclosure in any way.

Example 1

An exemplary camera system used in a live clinical workflow helped identify two wrong-patient errors in the first 8,000 images obtained by the camera system within the first seven months of deployment and demonstrated numerous cases where point-of-care photography provided image-related clinical context impacting diagnosis.

The camera system was supported by a Raspberry Pi Zero W controller enclosed in a 3D printed case and mounted on a portable digital X-ray machine. The camera system incorporated a wide-angle lens and was triggered by a pressure-sensitive mechanical switch that was mounted on the X-ray machine hand-switch so that the patient photo was obtained synchronously with the radiograph. To enhance security, photos were retrieved wirelessly from the camera by a storage silo (i.e., the PatCam Server (PS)) over a WPA2 secured wireless network hosted by the PS—thus eliminating any need for the camera to have credentials for logging into or sending photos to the PS. Upon successful retrieval of the photos at the PS, the copies local to the camera were deleted. The PS interacted with the PACS server using a wired Ethernet connection, separate from the secured wireless network used for the aforementioned photo retrieval. All local data containing private health information was automatically deleted daily.

It was clear to the radiologists that the errors identified using the camera system above would have been missed without the corresponding photographs. For one of the misidentified studies, the patient photo was used by a radiologist to confirm the error. Furthermore, the same photo was used by the X-ray technologists to find the correct patient. This is unprecedented since misfiled radiographs are usually discarded, implying that a misidentified patient underwent repeat imaging with its attendant radiation.

Example 2

In an observer study, radiologists interpreting portable radiographs, with and without the presence of synchronously obtained photographs, showed significantly increased confidence in interpretation with photographs. The results also showed that feeding tubes and endotracheal tubes were more accurately identified on radiographs when the photos were available during interpretation.

Example 3

Despite the Joint Commission mandated dual-identifier technique, wrong-patient errors still occur. In a retrospective conducted at Emory Healthcare, 67 wrong-patient errors were identified over a 3.5-year period. This search only identified errors that were discovered by radiologists after a report was generated and an addendum was subsequently issued containing either the phrase "wrong patient" or the phrase "incorrect patient." This is clearly the lower bound since many errors may have not been identified and those that were identified may not have been issued addenda with such phrases.

Example 4

Two pilot studies with simulated wrong-patient errors were conducted at Emory University to validate the effect of patient photographs on radiologists' interpretation—one study with ten radiologists and a second study with five radiologists. In a third study, 90 radiologist examiners were asked to interpret ten pairs of portable chest radiographs either with or without the presence of photographs. The key finding of these three studies was that the presence of photographs of the patient (e.g., the patient's face and chest) at the time of interpretation of portable chest radiographs significantly increased the detection rate of simulated wrong-patient errors. In the first study, with a set of 20 purportedly paired patient radiographs, the radiologists detected wrong-patient errors 12.5% of the time; after introduction of the photographs shown in tandem with the 20 pairs of purportedly paired patient radiographs, the error detection rate increased to 64% (p=0.0003). Similarly, in the second study, the wrong-patient error detection rate increased from 0% to 94.4% (p<0.0001). In the larger study with 90 radiologists, the detection rate of simulated wrong patient errors increased from 31% to 77% (p=0.006) following the introduction of photographs.

These studies led to an intriguing and unexpected finding: showing photographs of the patient led to a decreased time in interpretation of the radiograph. In the ten-radiologist study, the interpretation time for 20 pairs of radiographs decreased from 35.73 to 26.51 minutes (p=0.1165), and in the five-radiologist study, it decreased from 26.45 to 20.55 minutes (p=0.1911). These studies were designed to evaluate changes in error detection rates and not to determine if interpretation time would change. However, this unexpected finding was very intriguing and indicated that the interpretation time of radiographs may decrease as a result of the interpreting radiologists being presented with novel and salient clinical information via the photographs.

What is claimed is:

1. A method, comprising:
obtaining a photograph and a medical image, the photograph and the medical image being captured simultaneously, the photograph and the medical image capturing the same patient;
automatically co-registering the photograph and the medical image by maximizing mutual information between the photograph and the medical image;
obtaining located common features by automatically locating features that are captured in both the photograph and the medical image based on maximized mutual information between the photograph and the medical image, wherein the medical image comprises a radiographic image, an ultrasound image, a computed tomography image, a scintigraphy image, a single-photon emission computed tomography image, a positron emission tomography image, or a magnetic resonance imaging image;
automatically highlighting the located common features within the photograph or the medical image; and
displaying a highlighted representation of the located common features within the photograph or the medical image on a user interface.

2. The method of claim 1, wherein the medical image comprises a radiograph.

3. The method of claim 1, wherein the photograph comprises an infrared image.

4. The method of claim 1, wherein the photograph comprises a visible light image.

5. The method of claim 1, wherein automatically locating the features captured in both the photograph and the medical image utilizes region-based correlation.

6. The method of claim 1, wherein highlighting the located features comprises modifying a color of the located features as depicted in the image or the medical image.

7. The method of claim 1, wherein the located features correspond to external, non-anatomic features.

8. The method of claim 1, wherein the photograph and the medical image are captured simultaneously via operation of a single trigger.

9. The method of claim 1, wherein automatically co-registering the photograph and the medical image comprises:
identifying rotation, translation, scale, or skew correction based on maximized mutual information between the photograph and the medical image; and
adjusting the photograph relative to the medical image based upon the identified rotation, translation, scale, or skew correction.

10. The method of claim 1, further comprising displaying a co-registered representation of the photograph and the medical image on the user interface in combination with the highlighted representation of the located common features.

11. A method, comprising:
obtaining a photograph and a medical image, the photograph and the medical image being captured simultaneously, the photograph and the medical image capturing the same patient;
automatically co-registering the photograph and the medical image utilizing a machine learning model;
obtaining located common features by automatically locating features that are captured in both the photograph and the medical image, wherein the medical image comprises a radiographic image, an ultrasound image, a computed tomography image, a scintigraphy image, a single-photon emission computed tomography image, a positron emission tomography image, or a magnetic resonance imaging image;
automatically highlighting the located common features within the photograph or the medical image; and
displaying a highlighted representation of the located common features within the photograph or the medical image on a user interface.

12. The method of claim 11, wherein the medical image comprises a radiograph.

13. The method of claim 11, wherein the photograph comprises an infrared image.

14. The method of claim 11, wherein automatically locating the features captured in both the photograph and the medical image utilizes region-based correlation.

15. The method of claim 11, wherein highlighting the located features comprises modifying a color of the located features as depicted in the image or the medical image.

16. The method of claim 11, wherein the located features correspond to external, non-anatomic features.

17. The method of claim 11, wherein the photograph and the medical image are captured simultaneously via operation of a single trigger.

18. The method of claim 11, wherein automatically co-registering the photograph and the medical image comprises:
identifying rotation, translation, scale, or skew transformation between the photograph and the medical image; and
adjusting the photograph relative to the medical image based upon the identified rotation, translation, scale, or skew transformation.

19. The method of claim 11, further comprising displaying a co-registered representation of the photograph and the medical image on the user interface in combination with the highlighted representation of the located common features.

20. One or more hardware storage devices storing instructions that are executable by one or more processors of a system to configure the system to:
obtain a photograph and a medical image, the photograph and the medical image being captured simultaneously, the photograph and the medical image capturing the same patient;
automatically co-register the photograph and the medical image by maximizing mutual information between the photograph and the medical image;
obtain located common features by automatically locating features captured in both the photograph and the medical image based on maximized mutual information between the photograph and the medical image, wherein the medical image comprises a radiographic image, an ultrasound image, a computed tomography image, a scintigraphy image, a single-photon emission computed tomography image, a positron emission tomography image, or a magnetic resonance imaging image;
automatically highlight the located common features within the photograph or the medical image; and
display a highlighted representation of the located common features within the photograph or the medical image on a user interface.

* * * * *